(12) United States Patent
Gotta et al.

(10) Patent No.: US 9,024,045 B2
(45) Date of Patent: May 5, 2015

(54) PROCESS FOR PREPARING STYRENE DERIVATIVES

(71) Applicant: Saltigo GmbH, Langenfeld (DE)

(72) Inventors: Matthias Gotta, Burscheid (DE); Bernd Wilhelm Lehnemann, Cologne (DE); Axel Von Wangelin Jacobi, Regensburg (DE); Samet Guelak, Cologne (DE)

(73) Assignee: Saltigo GmbH, Leverkusen (DE)

( * ) Notice: Subject to any disclaimer, the term of this patent is extended or adjusted under 35 U.S.C. 154(b) by 0 days.

(21) Appl. No.: 13/907,228

(22) Filed: May 31, 2013

(65) Prior Publication Data

US 2013/0324745 A1    Dec. 5, 2013

(30) Foreign Application Priority Data

Jun. 4, 2012  (EP) .................................... 12170697

(51) Int. Cl.

| | | |
|---|---|---|
| *C07D 317/46* | (2006.01) | |
| *C07C 209/74* | (2006.01) | |
| *C07C 17/278* | (2006.01) | |
| *C07C 41/30* | (2006.01) | |
| *C07C 2/66* | (2006.01) | |
| *C07D 317/50* | (2006.01) | |
| *C07B 37/04* | (2006.01) | |
| *C07B 49/00* | (2006.01) | |
| *C07C 209/68* | (2006.01) | |
| *C07C 1/32* | (2006.01) | |
| *C07C 17/263* | (2006.01) | |
| *C07D 309/12* | (2006.01) | |
| *C07D 317/54* | (2006.01) | |
| *C07D 319/06* | (2006.01) | |
| *C07C 213/08* | (2006.01) | |

(52) U.S. Cl.

CPC ............ *C07D 317/46* (2013.01); *C07C 209/74* (2013.01); *C07C 17/278* (2013.01); *C07C 41/30* (2013.01); *C07C 2/66* (2013.01); *C07D 317/50* (2013.01); *C07B 37/04* (2013.01); *C07B 49/00* (2013.01); *C07C 209/68* (2013.01); *C07C 1/326* (2013.01); *C07C 17/2632* (2013.01); *C07C 2101/02* (2013.01); *C07C 2101/14* (2013.01); *C07D 309/12* (2013.01); *C07D 317/54* (2013.01); *C07D 319/06* (2013.01); *C07C 213/08* (2013.01)

(58) Field of Classification Search

CPC ........................................................ C07D 317/46
USPC ............................................................ 549/434
See application file for complete search history.

(56) References Cited

U.S. PATENT DOCUMENTS 7,674,507 B2   3/2010 Lietzau et al.

OTHER PUBLICATIONS

Niwa, Palladium-Catalyzed Benzylic Arylation of N-Benzylxanthone Imine:, Organic Letters, 2008. vol. 10, No. 20, pp. 4689-4691, American Chemical Society.
Torberg, et al., "Improved Palladium-Catalyzed Sonogashira Coupling Reactions of Aryl Chlorides", Chem. Eur. J. 2009, 15 1329-1336, Wiley-VCH Verlag GmbH & Co, KGaA, Weinheim, Germany.
Furstner et al., "Iron-Catalyzed Cross-Coupling Reactions of Alkyl-Grignard Reagents with Aryl Chlorides, Tosylates, and Triflates", Angew. Chem. Int. Ed. 2002, 41, No. 4, Wiley-VCH Verlag GmbH, 69451 Weinheim, Germany.
Nakamura et al., "Iron-Catalyzed Cross-Coupling of Primary and Secondary Alkyl Halides with Aryl Grignard Reagents", J. Am. Chem. Soc., 2004, 126, 3686-3687, American Chemical Society.
Dohle et al., "Fe(III)-Catalyzed Cross-Coupling Between Functionalized Arylmagnesium Compounds and Alkenyl Halides", Synlett 2001, No. 12, 30 11 2001, Georg Thieme Verlag Stuttgart, New York.
Cahiez et al., "Iron-Catalyzed Alkylations of Aromatic Grignard Reagents", Angew, Chem. Int. Ed. 2007, 46, 4364-4366, Wiley-VCH Verlag GmbH & Co., KGaA, Weinheim, Germany.
Tamura, et al., "Vinylation of Grignard Reagents, Catalysis by Iron", J. Am. Chem. Soc., 93:6, Mar. 24, 1971, 1487-1489.
Gulak et al., "Chlorostyrenes in Iron-Catalyzed Biaryl Coupling Reactions", Angew, Chem. Int. Ed., 2012, 51, 1357-1361, Wiley-VCH Verlag GmbH & Co., KGaA, Weinheim, Germany.
European Search Report from co-pending Application EP12170697.2 dated Sep. 21, 2012, 4 pages.

*Primary Examiner* — Taofiq A Solola

(57) ABSTRACT

A process is provided which allows the synthesis of a large number of styrene derivatives with formation of C—C bonds, with use being possible of economically advantageous substrates, readily available carbon nucleophiles, and both inexpensive and environmentally unproblematic catalyst systems, permitting reaction under mild conditions and a high compatibility with functional groups on the reactants involved.

17 Claims, No Drawings

PROCESS FOR PREPARING STYRENE DERIVATIVES

The invention provides a process for preparing styrene derivatives by transition metal-catalysed cross-coupling of chlorostyrenes with organomagnesium compounds in the presence of iron compounds.

Transition metal-catalysed cross-couplings are important synthesis tools in modern organic chemistry, though the majority of the known cross-coupling reactions use palladium complexes or nickel complexes as transition metal catalysts. Cross-coupling with chlorostyrenes, which are particularly advantageous both economically and environmentally, with substitution of the chlorine atom, is described only in a few sporadic cases—for example, as arylation of activated benzyl derivatives, by Niwa et al., Org. Lett. 2008, 10, 4639; as Sonogashira coupling with terminal alkynes, by Torborg et al., Chem. Eur. J. 2009, 15, 1329, and as Suzuki coupling with arylboronic acids, by Lietzau et al., WO 2006/125511, with all the reactions having proceeded with palladium catalysis. Moreover, the known reactions in this class either proved highly substrate-specific in relation to the coupling partner (for example, confined to CH-acidic benzyl derivatives or to terminal alkynes) or required complicated and costly boric acid derivatives as coupling partners. To obtain acceptable reactivity of the catalyst system, furthermore, it was necessary to use organic ligands in the form of phosphines or N-heterocyclic carbenes, which, however, are relatively expensive and are generally not recoverable. Cross-coupling with simple alkyl derivatives, in addition, was not possible using these catalysts.

Attempts have therefore been made to develop cross-coupling techniques which permit not only the use of the economically advantageous chlorostyrenes but also the use of readily available carbon nucleophiles, such as Grignard compounds, for example, the intention being not least to employ inexpensive, readily available and non-toxic catalysts and ligands.

Iron compounds are available at substantially more favourable prices than palladium, and they are far less toxic than nickel compounds and offer distinct advantages from an environmental standpoint over copper-based catalyst systems. The purification of wastewaters, in particular, is facilitated significantly.

Back at the beginning of the 1970s it was found that iron salts are able to catalyse the cross-coupling of vinyl halides with alkyl-Grignard compounds (Kochi et al., J. Am. Chem. Soc. 1971, 1487), but this reaction found only very limited application in the subsequent 30 years, on account of the narrow scope for its application, until Knochel, Fürstner, Cahiez and Nakamura succeeded in applying iron-catalysed cross-couplings with aid from nitrogen-containing additives such as N-methylpyrrolidone or N,N,N',N'-tetramethylethylenediamine (TMEDA), for example, over a greater breadth of substrates (e.g. Fürstner et al., Angew. Chem. Int. Ed. 2002, 41, 609; Nakamura et al., J. Am. Chem. Soc. 2004, 3686; Knochel et al., Synlett 2001, 1901; Cahiez et al., Angew. Chem. Int. Ed. 2007, 4364). These reactions are distinguished by especially mild reaction conditions (−20° C. to +35° C.), high functional-group compatibility (e.g. methyl esters, amines) and short reaction times (usually less than two hours). Another reason why these reactions are of particular interest for industrial application is that as a general rule they do not need expensive and sensitive phosphine ligands or carbene ligands, as is often the case with nickel-based and palladium-based catalyst systems, especially if inexpensive aryl chlorides serve as coupling partners, rather than the aryl bromides or aryl iodides.

These iron-catalysed cross-couplings, however, were considered to be confined to electron-deficient chlorostyrenes where the aryl ring had electron-withdrawing carboxyl, cyano, trifluoro-methyl or sulphoxyl substituents, or to electron-deficient, chlorinated, heteroaromatic compounds. Fürstner et al. taught, accordingly, the use of the more reactive, although more difficult to synthesize, aryl triflates in the case of electron-donating substituents on the aromatic moiety, such as methyl, methoxy, aryl, or aryloxy. The cross-coupling of chlorostyrenes, which are relatively electron-rich on account of the alkenyl group, with organomagnesium compounds was neither performed nor attempted.

The object of the present invention was to provide a process for preparing styrene derivatives by cross coupling, allowing the use of inexpensive and eco-friendly iron catalysts, in order to link chlorostyrenes with organomagnesium compounds, which are readily available and can be prepared with great substrate breadth.

The present object has been achieved through the surprising finding that in spite of the electron-donating effect of the alkenyl group, chlorostyrenes can be cross-coupled with magnesium organyls in the presence of iron compounds in tandem with the possibility, typically, of using the known mild conditions of iron catalysis. As a result, a new efficient, inexpensive and eco-friendly access is provided to a class of substance which was hitherto accessible only at substantially greater cost and complexity.

The invention accordingly provides a process for preparing organic compounds of the general formula (I)

in which
i is 0, 1, 2 or 3, preferably 0 or 1,
j is 0, 1, 2, 3 or 4, preferably 0 or 1,
$R^2$ independently at each occurrence is selected from unsubstituted or fluoro-, $NR^4{}_2$-, $C_1$-$C_6$-alkyl- or $C_1$-$C_6$-alkoxy-substituted $C_1$-$C_6$-alkyl, $C_6$-$C_{10}$-aryl or $C_7$-$C_{11}$-aralkyl, it being possible for each $R^4$ independently to be $C_1$-$C_6$-alkyl, $C_7$-$C_{10}$-aryl or $C_7$-$C_{11}$-aralkyl,
$R^3$ independently at each occurrence is selected from fluoro, chloro, $NR^4{}_2$, unsubstituted or $NR^4{}_2$- or $C_1$-$C_6$-alkoxy-substituted $C_1$-$C_6$-alkyl, and also unsubstituted or fluoro-, $NR^4{}_2$- or $C_1$-$C_6$-alkoxy-substituted $C_1$-$C_6$-alkoxy or $C_7$-$C_{11}$-aralkyl, where each $R^4$ independently has the definitions indicated above, and where two or more of the substituents $R^2$ and/or $R^3$ together form an aromatic, heteroaromatic, aliphatic or heteroaliphatic ring system, subject to the condition that the vinyl function which carries the radical $R^2$ is not part of such a ring system if that system is aromatic or heteroaromatic, and
$R^1$ is an unsubstituted or fluoro-, $C_1$-$C_6$-alkoxy-, or $NR^4{}_2$-substituted $C_1$-$C_{15}$-alkyl, $C_3$-$C_7$-cycloalkyl, $C_2$-$C_{15}$-alkenyl, $C_3$-$C_7$-cycloalkenyl, $C_2$-$C_{15}$-alkynyl, $C_1$-$C_6$-alkoxy, $C_7$-$C_{15}$-aralkyl or $C_6$-$C_{10}$-aryl radical, or is a correspondingly substituted or unsubstituted aliphatic or aromatic $C_3$-$C_{12}$ heterocycle, with each $R^4$ independently having the definitions indicated above,
by reacting chlorostyrenes of the general formula (II)

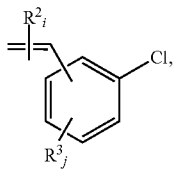

(II)

in which
$R^2$, $R^3$, i and j have the definitions described for formula (I),
with organomagnesium compounds of the formal composition (III)

$$[M^+]_n[R_mMgX_kY_l]$$ (III), in which
$R^1$ has the definition described for formula (I),
M is lithium, sodium or potassium,
X is fluoro, chloro, bromo or iodo, preferably chloro or Br chloro, bromo, very preferably bromo,
Y is fluoro, chloro, bromo or iodo, preferably chloro or Br chloro, bromo, very preferably bromo,
n is 0, 1, 2, 3 or 4, preferably 0 or 1, very preferably 0,
m is 1, 2, 3, 4, 5 or 6, preferably 1 or 2, very preferably 1,
k is 0, 1, 2, 3 or 4, preferably 0, 1 or 2, very preferably 0 or 1,
l is 0, 1, 2, 3 or 4, preferably 0, 1 or 2, very preferably 0 or 1,
and at the same time the relation $n+2=m+k+l$ is valid,
characterized in that the reaction is carried out in the presence of iron compounds, preferably iron(II) or iron(III) compounds.

In one preferred embodiment i is 0 or 1. In another preferred embodiment j is 0.1 or 2, and in a particularly preferred embodiment i is 0 or 1 and j is 0.1 or 2.

In one preferred embodiment $R^2$ is selected independently from $C_1$-$C_6$-alkyl, $C_6$-$C_{10}$-aryl, and $C_7$-$C_{11}$-aralkyl, with methyl, ethyl or propyl, phenyl and naphthyl representing particularly preferred embodiments.

In one preferred embodiment $R^3$ independently at each occurrence is selected from chloro, $NR^4_2$, where each $R^4$ independently can be $C_1$-$C_6$-alkyl, $C_7$-$C_{10}$-aryl or $C_7$-$C_{11}$-aralkyl, preferably $C_1$-$C_6$-alkyl, more preferably methyl, ethyl or propyl, $C_1$-$C_6$-alkoxy, $C_6$-$C_{10}$-aryl, more preferably phenyl or naphthyl and $C_7$-$C_{11}$-aralkyl.

In the embodiment in which two or more of the substituents $R^2$ and/or $R^3$ together form a heteroaromatic or heteroaliphatic ring system preferred heteroatoms of the heteroaliphatic or (hetero)aralyphatic ring system are nitrogen, oxygen or sulphur, and especially oxygen, and in the case of the heteroaralphatic ring system the heteroatoms are present preferably in the aliphatic part of the ring system.

For the purposes of the present invention, the aliphatic or aromatic heterocyclic $C_3$-$C_{12}$ radical in the case of the radical $R^1$ comprises monocyclic and polycyclic compounds in which there is at least one ring as heterocycle and further rings optionally present are constructed from hydrocarbons and/or heteroatoms, with the heteroatoms of the aliphatic or aromatic heterocyclic $C_3$-$C_{12}$ radical being preferably selected from oxygen, nitrogen and/or sulphur.

In one preferred embodiment $R^1$ is an unsubstituted or fluoro-, $C_1$-$C_4$-alkoxy- or $NR^4_2$-substituted $C_1$-$C_{11}$-alkyl, $C_3$-$C_7$-cycloalkyl, $C_2$-$C_{11}$-alkenyl, $C_3$-$C_7$-cycloalkenyl, $C_2$-$C_{11}$-alkynyl, $C_7$-$C_{12}$-aralkyl or $C_6$-$C_{10}$-aryl radical, or a correspondingly substituted or unsubstituted aliphatic or aromatic $C_3$-$C_8$ heterocycle, with each $R^4$ independently being $C_1$-$C_6$-alkyl. The aliphatic or aromatic heterocyclic $C_3$-$C_8$ radical in this case comprises monocyclic and polycyclic compounds in which there is at least one ring as heterocycle and further rings optionally present are constructed from hydrocarbons and/or heteroatoms, with the heteroatoms of the aliphatic or aromatic heterocyclic $C_3$-$C_8$ radical consisting of oxygen and/or nitrogen, preferably of oxygen.

Chlorostyrenes of the general formula (II) are available commercially or preparable by means of known methods such as Wittig olefinization or Heck reaction, for example. In accordance with the invention they are preferably used individually, although the use of a mixture of two or more chlorostyrenes is also possible. The alkenyl group of the chlorostyrene here is positioned ortho, meta or para, preferably ortho or para and more preferably ortho to the chlorine substituent.

Examples of chlorostyrenes of the formula (II) are 2-chlorostyrene, 3-chlorostyrene, 4-chlorostyrene, 4-chlorostilbene, 1-chloro-4-isopropenylbenzene, 1-chloro-3-isopropenylbenzene, 4-N,N-dimethylamino-2-chlorostyrene, 3-methoxy-2-chlorostyrene, 2-chloro-4,5-methylenedioxystyrene, 2-chloro-4,5-dimethoxystyrene, 4-(4-chlorophenyl-3-methylprop-1-en)-1-ylstyrene, 2,4-dichlorostyrene and 3-N,N-dimethylamino-2-chlorostyrene.

The preparation of the organomagnesium compound (III) is familiar to the skilled person, for example by Grignard reaction of an organic halogen compound R—X (where X is fluoro, chloro, bromo or iodo) with elemental magnesium, under suitable conditions, including by halogen-metal exchange or deprotonation, optionally with addition of auxiliaries such as lithium chloride, for example, or by transmetallation of other organometallic compounds—organolithium compounds, for example—with suitable magnesium compounds, examples being magnesium salts or Grignard compounds. For the process of the invention, preference is given to using organomagnesium chlorides $R^1MgCl$ or organomagnesium bromides $R^1MgBr$, very preferably organomagnesium bromides $R^1MgBr$, where $R^1$ has the definition described for formula (I).

Examples of suitable organomagnesium compounds are organomagnesium bromides such as, for example, nonylmagnesium bromide, undecylmagnesium bromide, 2-ethylhexyl-1-magnesium bromide, cyclopropylmagnesium bromide, 2-cyclohexylethyl-1-magnesium bromide, 2-propylenedioxyethyl-1-magnesium bromide, 9-decen-1-ylmagnesium bromide, 6-tetrahydropyran-2-oxyhexyl-1-magnesium bromide, 4-(N,N-dimethylamino)phenylmagnesium bromide, 4'-fluorobiphenyl-4-magnesium bromide, 4-fluorophenylmagnesium bromide, 4-methoxyphenylmagnesium bromide, 4-fluoro-3-methylphenylmagnesium bromide and thiophen-2-ylmagnesium bromide; and also bis(4-methoxyphenyl)magnesium, bis(4-methoxyphenyl)-magnesium-lithium chloride complex, 4-methoxyphenylmagnesium chloride-lithium chloride complex and lithium trihexylmagnesate.

The preferred molar ratio of employed chlorostyrene of the formula (II) to organomagnesium compound (III) is from 10:1 to 1:10, more preferably from 3:1 to 1:3 and very preferably from 3:2 to 2:3.

The process of the invention is carried out customarily in a dry aprotic organic solvent or in a mixture of one or more of these solvents. In one preferred embodiment the solvent comprises or consists of one or more ethers, preferably selected from tetrahydrofuran (THF), 2-methyltetrahydrofuran (2-methyl-THF), 1,4-dioxane, methyl tert-butyl ether (MTBE), diethyl ether, 1,2-dimethoxyethane (DME, glyme), diisopropyl ether (DIPE), dipropyl ether, dibutyl ether, cyclopentyl methyl ether, diethylene glycol dimethyl ether (diglyme), triethylene glycol dimethyl ether(triglyme), tetraethylene glycol dimethyl ether(tetraglyme) and diethylene glycol dibutyl ether, with THF being particularly preferred.

In one preferred embodiment the reaction is carried out in a solvent which comprises one or more nitrogen-containing additives selected from trialkylamines, preferably triethylamine, ethyldiisopropyl amine or N,N,N',N'-tetramethylethylenediamine (TMEDA), N-containing aliphatic heterocycles, preferably 1,4-diazabicyclo[2.2.2]octane (DABCO) or sparteine, alkylamides, cyclic alkylamides (lactams), preferably N-methyl-2-pyrrolidone (NMP), cycloalkylamines, preferably 1,2-diaminocyclohexane (DACH), cycloalkyldiamines, alkylimines, cycloalkylimines, aniline derivatives, preferably N,N-dimethylaniline, ureas, urethanes or nitrogen-containing heteroaromatics, preferably pyridine or phenanthroline. With particular preference N-methyl-2-pyrrolidine (NMP) is added. The additive may also take on the role of a cosolvent.

In the process of the invention the fraction of the nitrogen-containing additive relative to the amount of solvent used is 0.1 to 50 vol %, more preferably 1 to 20 vol %, very preferably 5-15 vol %.

The iron compound in the case of the present invention may be used in any desired oxidation state, with preference being given for practical reasons to compounds with iron in the +2 or +3 oxidation state—for example, iron(II) chloride, iron (III) chloride, iron(H) acetylacetonate, iron(III) acetylacetonate, iron(II) acetate, iron(III) acetate, iron(III) bromide, iron (III) bromide, iron(II) fluoride, iron(III) fluoride, iron(II) iodide, iron(III) iodide, iron(II) sulphate, iron(II) trifluoroacetate, iron(II) trifluoromethanesulphonate, iron(III) trifluoromethanesulphonate, iron(III) chloride-TMEDA complex or a mixture of these compounds.

The iron compound may be used in substoichiometric, stoichiometric or superstoichiometric amount, use being made preferably of a substoichiometric amount, more preferably an amount of 0.01 to 20 mol %, and very preferably an amount of 0.01 to 10 mol %, based on the compound of the general formula (II).

The process of the invention is carried out customarily at a reaction temperature in the range from −40° C. to +100° C., preferably in the range from 0 to +80° C., more preferably in the range from +20° C. to +80° C. A further embodiment according to the invention is the reaction regime under irradiation by microwaves, which is associated with the advantage of more rapid conversion.

One preferred embodiment sees first a portion of the organomagnesium compound being added to the mixture of iron compound, solvent and nitrogen-containing additive or cosolvent, and the remaining fraction of organomagnesium compound being slowly added dropwise.

In another embodiment the organomagnesium compound is added all at once. The latter may be advantageous especially in the case of fluorine-substituted organic radicals of the organomagnesium compound.

Through the process of the invention it has therefore become possible for the first time to couple a multiplicity of differently substituted chlorostyrenes with organomagnesium compounds.

EXAMPLES

Example 1

Coupling of 2-chlorostyrene with 4-dimethylaminophenylmagnesium bromide

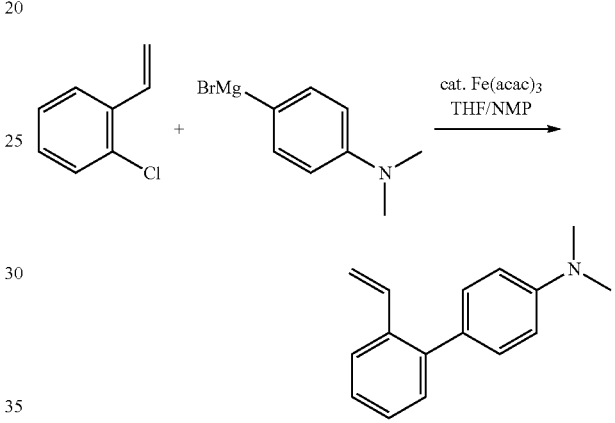

Under inert gas 17.7 mg (5 mol %, 0.05 mmol) of iron(II) acetylacetonate were taken up in 4.4 ml of a mixture of tetrahydrofuran and NMP (v/v 10:1). At 30° C. 138.6 mg (1.0 mmol) of 2-chlorostyrene were added. Then 3 ml of a 0.5 M solution of 4-dimethylaminophenylmagnesium bromide in THF (about 1.5 mmol) were added. After two-hour stirring the reaction mixture was rendered aqueous with 5 ml of saturated sodium carbonate solution and extracted with three times 5 ml of ethyl acetate. The combined organic phases were dried over magnesium sulphate and concentrated on a rotary evaporator and the crude product obtained was analysed by gas chromatography. The yield was 146 mg (0.65 mmol, 65% of theory) of 2'-vinyl-4-dimethylaminobiphenyl.

Examples 2 to 15

Further couplings of chlorostyrenes with aryl-Grignard compounds were conducted, the procedure being analogous to that of example 1, but using the reactants listed in table 1. The individual yields are not optimized.

TABLE 1

| Example No. | Chlorostyrene | Grignard compound | Product | Yield (% of theory) |
|---|---|---|---|---|
| 2 | 1-Chloro-4-isopropenylbenzene | 4-Fluorophenyl-magnesium bromide | 4-Fluoro-4'-isopropenyl biphenyl | 93 |

TABLE 1-continued

| Example No. | Chlorostyrene | Grignard compound | Product | Yield (% of theory) |
|---|---|---|---|---|
| 3 | 2-Chlorostyrene | 4-Methoxyphenyl-magnesium bromide | 4-Methoxy-2'-vinyl-biphenyl | 71 |
| 4 | 2-Chlorostyrene | 4-Fluorophenyl-magnesium bromide | 4-Fluoro-2'-vinylbiphenyl | 83 |
| 5 | 4-Dimethylamino-2-chloro-styrene | 4-Fluorophenyl-magnesium bromide | 3-Dimethylamino-4'-fluoro-2-vinylbiphenyl | 72 |
| 6 | 2-Chlorostyrene | 4-Fluoro-3-methylphenyl-magnesium bromide | 4-Fluoro-3-methyl-4'-vinylbiphenyl | 83 |
| 7 | 2-Chloro-3-methoxystyrene | 4-Methoxyphenyl-magnesium bromide | 2,4'-Dimethoxy-6-vinylbiphenyl | 91 |
| 8 | 2-Chloro-3-methoxystyrene | 4-Fluorophenyl-magnesium bromide | 2-Methoxy-4'-fluoro-2-vinylbiphenyl | 70 |
| 9 | 2-Chloro-3-methoxystyrene | 4-Dimethylaminophenyl-magnesium bromide | 2'-Methoxy-4-dimethyl-amino-6'-vinylbiphenyl | 73 |
| 10 | 2-Chlorostyrene | 4-Trifluoromethoxy-phenylmagnesium bromide | 4-Trifluoromethoxy-2'-vinylbiphenyl | 83 |
| 11 | 2-Chlorostyrene | 1,3-Benzo-dioxol-5-yl-magnesium bromide | 5-(2-Vinylphenyl)-benzo[d][1,3]dioxole | 82 |
| 12 | 2-Chloro-4,5-dimethoxystyrene | 1,3-Benzo-dioxol-5-yl-magnesium bromide | 5-(4,5-Dimethoxy-2-vinyl-phenyl)benzo[d][1,3]-dioxole | 69 |
| 13 | 1-Chloro-3-isopropenylbenzene | 4-Fluorophenyl-magnesium bromide | 4-Fluoro-3'-isopropenyl biphenyl | 85 |
| 14 | 2,4-Dichlorostyrene | Phenylmagnesium bromide | 5-Chloro-2-vinylbiphenyl | 69 |
| 15 | 2-Chlorostyrene | Phenylmagnesium bromide | 2-Vinylbiphenyl | 89 |

Comparative Examples 1 to 3

The coupling of electron-rich aryl chlorides with aryl-Grignard compounds was attempted, the procedure being analogous to that of inventive example 1 but with the reactants listed in table 2. It was found that in the absence of the alkenyl group there is no coupling.

TABLE 2

| Comparative example No. | Grignard compound | Product | Yield (% of theory) |
|---|---|---|---|
| 1 | Chlorobenzene | Phenylmagnesium chloride | Biphenyl | 1 |
| 2 | 2-Chloroanisole | Phenylmagnesium chloride | 2-Methoxybiphenyl | 0 |
| 3 | 2-Chlorotoluene | Phenylmagnesium chloride | 2-Phenyltoluene | 0 |

Examples 16 to 26

Couplings of chlorostyrenes with alkyl-Grignard compounds were conducted, the procedure being analogous to that of example 1, but using the reactants listed in table 3. The individual yields are not optimized.

TABLE 3

| Example No. | Chlorostyrene | Grignard compound | Product | Yield (% of theory) |
|---|---|---|---|---|
| 16 | 2-Chlorostyrene | 1-Decylmagnesium bromide | 2-Decylstyrene | 94 |
| 17 | 2-Chlorostyrene | 1-Undecylmagnesium bromide | 2-Undecylstyrene | 85 |
| 18 | 4-Isopropenyl-chlorobenzene | 1-Decylmagnesium bromide | 1-Isopropenyl-4-decylstyrene | 71 |
| 19 | 4-Isopropenyl-chlorobenzene | 1-Undecylmagnesium bromide | 1-Isopropenyl-4-undecylstyrene | 70 |

TABLE 3-continued

| Example No. | Chlorostyrene | Grignard compound | Product | Yield (% of theory) |
|---|---|---|---|---|
| 20 | 2-Chlorostyrene | 2-Ethylhexyl-1-magnesium bromide | 2-(2-Ethylhexyl)-styrene | 80 |
| 21 | 2-Chlorostyrene | 2,2-(Propylenedioxy)ethyl-1-magnesium bromide | 2-(2,2-Propylene-dioxy)ethylstyrene | 97 |
| 22 | 2-Chlorostyrene | Cyclopropylmagnesium bromide | 2-Cyclopropylstyrene | 43 |
| 23 | 4-Chlorostilbene | Nonylmagnesium bromide | 4-Nonylstilbene | 60 |
| 24 | 4-(Propen-1-yl)-1-chlorobenzene | Nonylmagnesium bromide | 4-Nonyl-1-(propen-1-yl)-benzene | 63 |
| 25 | 2-Chlorostyrene | 2-Cyclohexylethyl-magnesium bromide | 2-(2-Cyclohexyl)-ethylstyrene | 75 |
| 26 | 2-Chlorostyrene | Dec-9-en-1-ylmagnesium bromide | 2-(Dec-9-en-1-yl)-styrene | 71 |
| 27 | 2-Chlorostyrene | [6-(Tetrahydro-2H-pyran-2-yl)oxy]hexylmagnesium bromide | 2-[6-(Tetrahydro-2H-pyran-2-yl)oxy]hexyl-styrene | 77 |
| 28 | 2-Chloro-3-methoxystyrene | Dec-9-en-1-ylmagnesium bromide | 2-(Dec-9-en-1-yl)-3-methoxystyrene | 70 |
| 29 | 2-Chloro-3-methoxystyrene | 2,2-(Propylenedioxy)-ethyl-1-magnesium bromide | 3-Methoxy-2-(2,2-propylenedioxy)ethyl-styrene | 70 |
| 30 | 2-Chloro-4,5-(methylenedioxy)-styrene | Decylmagnesium bromide | 2-Decyl-4,5-(methylenedioxy)-styrene | 73 |
| 31 | 2-Chloro-4,5-(methylenedioxy)-styrene | 2,2-(Propylenedioxy)-ethyl-1-magnesium bromide | 2-(2,2-Propylene-dioxy)ethyl-4,5-(methylenedioxy)-styrene | 82 |
| 32 | 4,5-Dimethoxy-2-chlorostyrene | 2,2-(Propylenedioxy)-ethyl-1-magnesium bromide | 2-(2,2-Propylene-dioxy)ethyl-4,5-di-methoxystyrene | 73 |
| 33 | 1-Chloro-4-[3-(4-chlorophenyl)-1-buten-1-yl]-benzene | Decylmagnesium bromide | 4-[3-(4-Chloro-phenyl)-1-buten-1-yl]-1-decylbenzene | 61 |

Example 34

The coupling of 2-chlorostyrene with decylmagnesium bromide was carried out as described in example 16, but at a reaction temperature of 55° C. This allowed the isolated yield of 2-decylstyrene to be raised to 97%.

Example 35

The coupling of 2-chlorostyrene and 4-fluorophenylmagnesium bromide was carried out as described in example 4, but the reaction mixture was subjected to microwaves from a commercial microwave apparatus. The reaction temperature rose to 80° C. in this case. After a reaction time of 15 minutes the yield was 85%.

The invention claimed is:

1. Process for preparing organic compounds of the general formula (I)

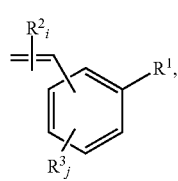

in which i is 0, 1, 2 or 3, j is 0, 1, 2, 3 or 4, $R^2$ independently at each occurrence is selected from unsubstituted or fluoro-, $NR^4{}_2$-, $C_1$-$C_6$-alkyl- or $C_1$-$C_6$-alkoxy-substituted $C_1$-$C_6$-alkyl, $C_6$-$C_{10}$-aryl or $C_7$-$C_{11}$-aralkyl, it being possible for each $R^4$ independently to be $C_1$-$C_6$-alkyl, $C_7$-$C_{10}$-aryl or $C_7$-$C_{11}$-aralkyl, $R^3$ independently at each occurrence is selected from fluoro, chloro, $NR^4{}_2$, unsubstituted or $NR^4{}_2$- or $C_1$-$C_6$-alkoxy-substituted $C_1$-$C_6$-alkyl, and also unsubstituted or fluoro-, $NR^4{}_2$- or $C_1$-$C_6$-alkoxy-substituted $C_1$-$C_6$-alkoxy or $C_7$-$C_{11}$-aralkyl, where each $R^4$ independently has the definitions indicated above, and where two or more of the substituents $R^2$ and/or $R^3$ together form an aromatic, heteroaromatic, aliphatic or heteroaliphatic ring system, subject to the condition that the vinyl function which carries $R^2$ is not part of such a ring system if that system is aromatic or heteroaromatic, and $R^1$ is an unsubstituted or fluoro-, $C_1$-$C_{10}$-alkyl-, $C_1$-$C_6$-alkoxy-, or $NR^4{}_2$-substituted $C_1$-$C_{15}$-alkyl, $C_3$-$C_7$-cycloakyl, $C_2$-$C_{15}$-alkenyl, $C_3$-$C_7$-cycloalkenyl, $C_2$-$C_{15}$-alkynyl, $C_1$-$C_6$-alkoxy, $C_7$-$C_{15}$-aralkyl or $C_6$-$C_{10}$-aryl radical, or is a correspondingly substituted or unsubstituted aliphatic or aromatic $C_3$-$C_{12}$ heterocycle, with each $R^4$ independently having the definitions indicated above, by reacting chlorostyrenes of the general formula (II)

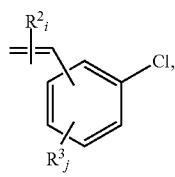

(II)

in which
$R^2, R^3$, i and j have the definitions described for formula (I),
with organomagnesium compounds of the formal composition (III)

$$[M^+]_n[R_mMgX_kY_l]$$ (III), in which
$R^1$ has the definition described for formula (I),
M is lithium, sodium or potassium,
X is fluoro, chloro, bromo or iodo,
Y is fluoro, chloro, bromo or iodo,
n is 0, 1, 2, 3 or 4,
m is 1, 2, 3, 4, 5 or 6,
k is 0, 1, 2, 3 or 4,
l is 0, 1, 2, 3 or 4,
and at the same time the relation $$n+2=m+k+l$$

is valid,
wherein the reaction is carried out in the presence of iron compounds.

2. Process according to claim 1, wherein $R^2$ independently at each occurrence is selected from $C_1$-$C_6$-alkyl, $C_6$-$C_{10}$-aryl, and $C_7$-$C_{11}$-aralkyl.

3. Process according to claim 1, wherein $R^3$ independently at each occurrence is selected from chloro, $NR^4_2$, where each $R^4$ independently has the definition according to claim 1, $C_1$-$C_6$-alkyl, $C_1$-$C_6$-alkoxy, $C_6$-$C_{10}$-aryl, and $C_7$-$C_{11}$-aralkyl.

4. Process according to claim 1, wherein $R^1$ is an unsubstituted or fluoro-, $C_1$-$C_4$-alkyl-, $C_1$-$C_4$-alkoxy- or $NR^4_2$-substituted $C_1$-$C_{11}$-alkyl, $C_3$-$C_7$-cycloalkyl, $C_2$-$C_{11}$-alkenyl, $C_3$-$C_7$-cycloalkenyl, $C_2$-$C_{11}$-alkynyl, $C_7$-$C_{12}$-aralkyl or $C_6$-$C_{10}$-aryl radical, or a correspondingly substituted or unsubstituted aliphatic or aromatic $C_3$-$C_8$ heterocycle, with each $R^4$ independently being $C_1$-$C_6$-alkyl.

5. Process according to claim 1, wherein the iron compound is selected from the group consisting of iron(II) chloride, iron(II) chloride, iron(II) acetylacetonate, iron(III) acetylacetonate, iron(II) acetate, iron(III) acetate, iron(II) bromide, iron(III) bromide, iron(II) fluoride, iron(III) fluoride, iron(II) iodide, iron(III) iodide, iron(II) sulphate, iron (II) trifluoroacetate, iron(II) trifluoromethanesulphonate, iron(III) trifluoromethanesulphonate, iron(III) chloride-TMEDA complex or a mixture of these compounds.

6. Process according to claim 5, wherein the reaction is carried out in the presence of a substoichiometric amount of the iron compound, based on the compound of the general formula (II).

7. Process according to claim 1, wherein the organomagnesium compounds are organomagnesium chlorides $R^1MgCl$ or organomagnesium bromides $R^1MgBr$, where $R^1$ has the definition indicated in claim 1.

8. Process according to claim 1, further comprising conducting the reaction in a solvent which comprises one or more nitrogen-containing additives selected from trialkylamines, N-containing aliphatic heterocycles, alkylamides, cyclic alkylamides (lactams), cycloalkylamines, cycloalkyldiamines, alkylimines, cycloalkylimines, anilines, ureas, urethanes or nitrogen-containing heteroaromatics.

9. Process according to claim 8, wherein an amount of the nitrogen-containing additive in the solvent is 0.1 to 50 vol %, based on the solvent used in the reaction.

10. Process according to claim 1, further comprising conducting the process in an aprotic organic solvent.

11. Process according to claim 1, wherein the reaction is carried out under irradiation with microwaves.

12. Process according to claim 1, wherein:
the iron compounds are iron(II) compounds or iron(III) compounds;
$R^1$ is an unsubstituted or fluoro-, $C_1$-$C_4$-alkyl-, $C_1$-$C_4$-alkoxy- or $NR^4_2$-substituted $C_1$-$C_{11}$-alkyl, $C_3$-$C_7$-cycloalkyl, $C_2$-$C_{11}$-alkenyl, $C_3$-$C_7$-cycloalkenyl, $C_2$-$C_{11}$-alkynyl, $C_7$-$C_{12}$-aralkyl or $C_6$-$C_{10}$-aryl radical, or a correspondingly substituted or unsubstituted aliphatic or aromatic $C_3$-$C_8$ heterocycle, with each $R^4$ independently being $C_1$-$C_6$-alkyl;
$R^2$ is selected from methyl, ethyl, propyl, phenyl, naphthyl, and $C_7$-$C_{11}$-aralkyl;
$R^3$ is selected from chloro, $NR^4_2$, where each $R^4$ independently has the definition according to claim 1, methyl, ethyl, propyl, $C_1$-$C_6$-alkoxy, phenyl, naphthyl and $C_7$-$C_{11}$-aralkyl; and
the organomagnesium compounds are organomagnesium chlorides $R^1MgCl$ or organomagnesium bromides $R^1MgBr$, where $R^1$ has the definition indicated in claim 1.

13. Process according to claim 12, wherein:
the reaction is carried out in the presence of an amount of 0.01 to 10 mol % of the iron compound, based on the compound of the general formula (II); and
the iron compounds are selected from the group consisting of iron(II) chloride, iron(III) chloride, iron(II) acetylacetonate, iron(III) acetylacetonate, iron(II) acetate, iron (III) acetate, iron(II) bromide, iron(III) bromide, iron(II) fluoride, iron(III) fluoride, iron(II) iodide, iron(III) iodide, iron(II) sulphate, iron(II) trifluoroacetate, iron (II) trifluoromethanesulphonate, iron(III) trifluoromethanesulphonate, iron(III) chloride-TMEDA complex or a mixture of these compounds.

14. Process according to claim 13, wherein:
the reaction is carried out in a solvent which comprises one or more nitrogen-containing additives selected from triethylamine, ethyldiisopropylamine, N,N,N',N'-tetramethylethylenediamine, 1,4-diazabicyclo[2.2.2]octane, sparteine, alkylamides, N-methyl-2-pyrrolidone, 1,2-diaminocyclohexane, cycloalkyldiamines, alkylimines, cycloalkylimines, N,N-dimethylaniline, ureas, urethanes, pyridine and phenanthroline; and
the amount of the nitrogen-containing additive in the solvent is 5-15 vol %, based on the solvent used in the reaction.

15. Process according to claim 14, wherein the solvent is selected from the group consisting of: tetrahydrofuran, 2-methyltetrahydrofuran, 1,4-dioxane, methyl tert-butyl ether, diethyl ether, 1,2-dimethoxyethane, diisopropyl ether, dipropyl ether, dibutyl ether, cyclopentyl methyl ether, diethylene glycol dimethyl ether, triethylene glycol dimethyl ether, tetraethylene glycol dimethyl ether, diethylene glycol dibutyl ether, dimethyl carbonate, 1,1,2,2-tetraethoxyethane, 1,1,2, 2-tetramethoxyethane or a mixture thereof.

16. Process according to claim 15, wherein:
a molar ratio of chlorostyrenes to organomagnesium compound is from 3:2 to 2:3; and the reaction is carried out under irradiation with microwaves at a reaction temperature in the range from 20° C. to 80° C.

17. Process according to claim 16, wherein the organomagnesium compound is added by a method comprising one of a) or b):
   a) a first a portion of the organomagnesium compound is added to a mixture of iron compound, solvent and nitrogen-containing additive or cosolvent, to produce a second mixture, and a remaining portion of the organomagnesium compound is slowly added dropwise to the second mixture; and
   b) all of the organomagnesium compound is added at once to a mixture of iron compound, solvent and nitrogen-containing additive or cosolvent, to produce a second mixture.

* * * * *